United States Patent [19]

Castrogiovanni et al.

[11] Patent Number: 5,145,670
[45] Date of Patent: Sep. 8, 1992

[54] NAIL ENAMELS CONTAINING GLYCERYL, GLYCOL OR CITRATE ESTERS

[75] Inventors: Anthony Castrogiovanni, Belford; Robert W. Sandewicz, Spotswood; Steven W. Amato, Fanwood, all of N.J.

[73] Assignee: Revlon, Inc., New York, N.Y.

[21] Appl. No.: 753,127

[22] Filed: Aug. 30, 1991

Related U.S. Application Data

[62] Division of Ser. No. 516,495, Apr. 30, 1990, Pat. No. 5,066,484.

[51] Int. Cl.⁵ .............................................. A61K 7/04
[52] U.S. Cl. ........................................ 424/61; 424/401
[58] Field of Search ............................. 424/61, 78, 401

[56] References Cited

U.S. PATENT DOCUMENTS

| | | | |
|---|---|---|---|
| 3,950,294 | 4/1976 | Connelly | 524/769 |
| 4,179,304 | 12/1979 | Rossomando | 424/61 |
| 4,601,901 | 7/1986 | Guillion | 424/61 |
| 4,749,564 | 6/1988 | Faryniarz | 424/61 |
| 4,814,015 | 3/1989 | Quinlan | 106/170 |
| 4,820,509 | 4/1989 | Yamazaki | 424/61 |
| 5,045,309 | 9/1991 | Dell'Aquila | 424/61 |

FOREIGN PATENT DOCUMENTS

| | | |
|---|---|---|
| 0170000 | 2/1986 | European Pat. Off. |
| 2569347 | 8/1984 | France . |
| 16910 | 1/1985 | Japan . |
| 2002795 | 2/1979 | United Kingdom . |

Primary Examiner—Thurman K. Page
Assistant Examiner—D. Gabrielle Phelan
Attorney, Agent, or Firm—Julie Blackburn

[57] ABSTRACT

Nail enamels containing a plasticizer component comprising one or more selected diesters or triesters, exhibit improved properties on wearing.

8 Claims, No Drawings

NAIL ENAMELS CONTAINING GLYCERYL, GLYCOL OR CITRATE ESTERS

This is a divisional of copending application Ser. No. 07/516,495 filed on Apr. 30, 1990 now U.S. Pat. No. 5,066,484.

BACKGROUND OF THE INVENTION

The present invention relates to nail enamels, also known as nail lacquers.

Nail enamels conventionally comprise a film forming component, which is frequently nitrocellulose, cellulose acetate butyrate, or a combination of one or both of those cellulosics with a polyurethane or other polymeric compound. Nail enamels have also traditionally included plasticizers, typically a phthalate such as dibutyl phthalate, or camphor, and have also typically included as a plasticizer and/or adhesion promoter a polymeric component formed by condensation polymerization of formaldehyde or other aldehyde, typically an aromatic sulfonamide-aldehyde condensation resin such as o, p-toluene sulfonamide formaldehyde resin.

It is desirable that a nail enamel contain reduced amounts of phthalates and aldehyde (e.g. formaldehyde) condensation products, in order to alleviate concerns that some wearers may be sensitized to phthalate or uncondensed aldehyde in the nail enamel. It is also desirable to reduce or eliminate volatile components such as camphor, since the volatility leads to loss of the component which causes variability in the performance of the nail enamel However, attempts to formulate such nail enamels have encountered difficulties because the nail enamel's desired properties such as long wear, high gloss, resistance to chipping on the nail, and compatibility with other nail enamel ingredients, are sensitive to changes in the ingredients in the nail enamel and to changes in the amounts of those ingredients. Therefore, there is still a need for a nail enamel formulation exhibiting satisfactory properties and containing little or no phthalate and/or aldehyde condensation products.

BRIEF SUMMARY OF THE INVENTION

Briefly stated, the present invention is a nail enamel comprising a film forming component, a solvent component, and a plasticizer component, wherein the plasticizer component comprises one or more compounds selected from the group consisting of compounds of formula (I) through (V):

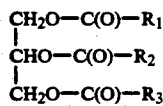
(I)

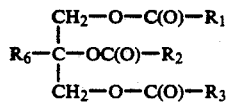
(II)

$R_1-C(O)-OCH_2-C(CH_3)_2CH_2O-C(O)R_2$ (III)

$R_1-C(O)-O(Y)_d-C(O)-R_2$ (IV)

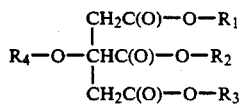
(V)

wherein $R_1$, $R_2$ and $R_3$ are the same or different and represent (i) linear or branched alkyl having 1 to 35 carbon atoms, cyclic alkyl having 3 to 8 carbon atoms, or linear or branched alkenyl having 2 to 35 carbon atoms, any of the foregoing being unsubstituted or substituted with one, two or three groups selected from the group consisting of —CN, —SCN, —OH, —SH, —NH$_2$, —CONH$_2$ and —NO$_2$;

(ii) —X—C(O)O—A or —X—O—C(O)—A in which X is a straight or branched alkyl or alkenyl bridge containing up to 8 carbon atoms or is a phenyl ring —CH$_6$H$_4$—, and A is phenyl, straight or branched alkyl having 1 to 35 carbon atoms, or straight or branched alkylene having 2 to 35 Carbon atoms, wherein when X or A is alkyl or alkenyl it is optionally substituted with -CN, —SCN, —NO$_2$, —OH, —SH, —NH$_2$ or —CONH$_2$ and wherein when X or A is phenyl it is optionally substituted with one, two or three substituents selected from the group consisting of —CN, —SCN, —Cl, —Br, —F, —OCH$_3$, —OC$_2$H$_5$, —OC$_6$H$_5$, —CH=CH$_2$, C$_{1-6}$alkyl, —CH$_2$CH=CH$_2$, —NO$_2$, —NH$_2$, —OH, —SH, and —SO$_2$NH$_2$;

(iii) a dimer or trimer acyl group; or (iv) BZ;

wherein BZ is a phenyl ring which is unsubstituted; or substituted with one or two groups of the formula —C(O)OR$_5$ wherein R$_5$ is straight or branched alkyl containing 1 to 35 carbon atoms, or straight or branched alkenyl containing 2 to 35 carbon atoms, the alkyl and alkenyl optionally substituted with —CN, —SCN, —NO$_2$, —OH, —SH, —NH$_2$ or —CONH$_2$; or R$_5$ is phenyl, unsubstituted or substituted with one, two, or three substituents selected from the group consisting of —CN, —SCN, —Cl, —Br, —F, —OCH$_3$, —OC$_2$H$_5$, —OC$_6$H$_5$, —CH=CH$_2$C$_{1-6}$alkyl, —CH$_2$CH=CH$_2$, —NO$_2$, —NH$_2$, —OH, —SH, and —SO$_2$NH$_2$;

and wherein d is 1 to 1,000;

each Y is ethoxy, isopropoxy or propoxy;

R$_4$ is H— or (Alk)—C(O)— wherein (Alk) is straight or branched alkyl containing 1 to 5 carbon atoms; and R$_6$ is straight or branched alkyl containing 1 to 18 carbon atoms or straight or branched alkenyl containing 2 to 18 Carbon atoms.

DETAILED DESCRIPTION OF THE INVENTION

As indicated, one notable aspect of the nail enamels of the present invention is the presence of one or more of the plasticizers defined above which are believed not to have been incorporated heretofore in nail enamels. One preferred type of plasticizer has the structure of formula (I)

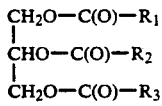

(I)

which compounds will be recognized as glyceryl triesters.

In the preferred embodiments of this invention, $R_1$, $R_2$ and $R_3$ are the same and the alkyl and alkylene substituents preferably contain up to 18 carbon atoms.

Examples of preferred compounds of formula (I) in which $R_1$, $R_2$ and $R_3$ are alkyl include glyceryl triacetate, glyceryl trioctanoate, glyceryl triundecanoate, and glyceryl tribehenate, the foregoing being the preferred examples when $R_1$, $R_2$ and $R_3$ are alkyl. Other suitable compounds in which $R_1$, $R_2$ and $R_3$ are alkyl or substituted alkyl include glyceryl tristearate, glyceryl triisostearate, glyceryl tri (hydroxystearate), glyceryl tripalmitate, glyceryl trimyristate, and glyceryl trilaurate. Examples of suitable compounds of the above formula (I) in which $R_1$, $R_2$ and $R_3$ are alkenyl or substituted alkenyl include glyceryl trioleate and glyceryl erucate, i.e. the triester of erucic acid. Other satisfactory compounds in which $R_1$, $R_2$ and $R_3$ are alkenyl include glyceryl triricinoleate and glyceryl triacetylricinoleate.

As indicated above, $R_1$, $R_2$ and $R_3$ can also be an optionally substituted phenyl ring. When the phenyl ring is unsubstituted, the preferred compound of formula (I) is glyceryl tribenzoate, which is a particularly preferred compound in the nail enamel compositions of the present invention.

Another optional substituent is a dimer or trimer acyl group, by which is meant a monoacyl derivative of a diacid or triacid formed by the addition reaction of two or three unsaturated carboxylic acids, each containing one, two or three vinylic bonds, across the respective vinylic bonds of each acid. Preferred acids are those containing 18 carbon atoms, such as oleic, linoleic, and linolenic. Preferred dimer and trimer acyl groups are those derived by dimerization or trimerization of any one of the foregoing acids. The remaining —COOH sites are preferably esterified with alkyl or alkylene containing 1 to 18 carbon atoms.

Other preferred types of plasticizer have the formula (II)

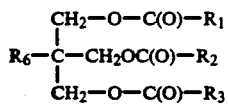

(II)

In the preferred compounds of formula (II), $R_1$, $R_2$ and $R_3$ are all unsubstituted phenyl. The compounds are trimethylolalkylbenzoates. For example, when $R_6$ is $CH_3CH_2$— the compounds are trimethylol propane compounds, e.g. trimethylol propane benzoates.

Other preferred types of plasticizers have the formula (III)

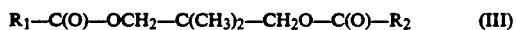

(III)

known as neopentylglycol esters, the more preferred of which are neopentyl benzoates.

The compounds of formula (V) are citrates. Examples of preferred citrates include those in which $R_4$ is H— or $C_{1-4}$ alkyl, and $R_1$, $R_2$ and $R_3$ are cyclohexyl, phenyl, or $C_{1-6}$ alkyl. More preferably, examples of compounds of formula (V) include acetyl tributyl citrate, acetyl triethyl citrate, acetyl tri-n-hexyl citrate, tribenzyl citrate, and tricyclohexyl citrate.

Other preferred plasticizers within the formula (IV) defined above have the following formulas (VI) through (IX):

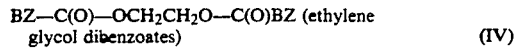

(IV)

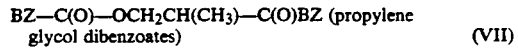

(VII)

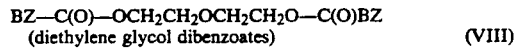

(VIII)

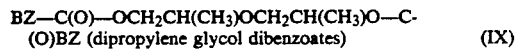

(IX)

Within the formula (IV) defined above, each alkoxy unit Y is preferably the same throughout the molecule, or is the same within a block of consecutive units Y comprising at least 5% of the total d of units.

It will be recognized that nail enamel compositions of the present invention include compositions containing more than one of the above defined compounds of formulas (I) through (V).

It will be readily apparent to those of ordinary skill in this art that the compounds of formulas (I) through (V) can readily be synthesized from known starting materials by employing straightforward esterifying conditions. Preferably, to make compounds of formula (I) through (IV), acid or an appropriately substituted acid $R_1COOH$, $R_2COOH$ and $R_3COOH$ (or, preferably, three molar equivalents of an acid $R_1COOH$ such as benzoic acid) are reacted with an appropriate dialcohol or trialcohol to esterify the alcoholic —OH groups with the acid. For instance, glyceryl tribenzoate in accordance with formula (I) is prepared by reacting glycerin with benzoic acid under esterifying conditions, in a molar ratio of benzoic acid to glycerin of at least 3:1.

Compounds of formula (V) can be made by reacting citric acid with compounds of the desired formula $R_1OH$, $R_2OH$ and $R_3OH$ (or three molar equivalents of compounds $R_1OH$) under esterifying conditions, and then optionally esterifying with an acid $R_4$—COOH when substitution at the $R_4$ position is desired.

Those skilled in this art will recognize that in many instances the desired substituents on compounds of formula (I)–(V) will already be in place on the carboxylic acid and alcohol intermediates which are reacted to form the desired ester. In other instances, it will be recognized that because of the particular desired substituent it will be more advantageous to employ a synthesis pathway in which the acid and/or the alcohol have fewer than all the desired substituents or have precursors of the desired substituents. In those latter instances, the desired substituents are added, or the precursors are converted to the desired substituents, after the esterification of the carboxylic acid and alcohol intermediates. For instance, when the desired ester will contain one or more amino substituents, it is preferred to form the ester with nitro substituents in place of the amino and then to reduce the nitro substituents to amino.

In some instances, the desired ester will be commercially available from chemical supply houses.

The skilled practitioner will recognize that the amount of the compound(s) of formulas (I) through (V)

in the nail enamel composition can vary depending on the precise combination of properties that are desired. The specific amount to employ can be readily ascertained by the nail enamel chemist, recognizing that too low an amount of the compounds (namely below about 0.5 wt. %) results in lack of flexibility and/or of adhesive properties in the dried film, whereas too high an amount of these compounds (namely above about 40 wt. %) results in an overly soft, slowly drying film. In general, satisfactory results can be obtained using about 0.5 to about 40 wt. % of the esters of any of the above formulas (I) through (V), preferably about 10 to about 25 wt. % thereof, and more preferably about 20 to about 25 wt. %.

The nail enamel compositions of the present invention will also contain a film-forming component, and a solvent component, and optionally a suspending component, pigment component, and preservative component.

One highly satisfactory film-forming component is nitrocellulose, which is the preferred film-forming component for compositions of this invention. Other satisfactory film-forming components include cellulose acetate butyrate, polyurethanes, and mixtures of polyurethanes with cellulose acetate butyrate or with nitrocellulose. Additionally, useful film-forming components can comprise acrylics, acrylates, polyurethanes, vinyls, acrylonitrile/butadiene copolymers, styrene/butadiene copolymers, epoxies, and any other polymer or copolymer capable of adaptation to a nail enamel system, such as the copolymers disclosed in U.S. Pat. No. 4,762,703, the disclosure of which is hereby incorporated by reference. The film-forming component should be present in an amount sufficient to provide a stable film upon the nail following the application of the nail enamel to the nail, but not so high a concentration that the nail enamel composition is unable to flow freely onto a brush and from the brush onto the nail. In general, amounts of the film-forming component of about 10 to about 40 wt. %, and more preferably about 15 to about 20 wt. %, are satisfactory.

The solvent component should be inert to the user's nail and to the other components of the nail enamel composition, should be capable of dissolving or dispersing the other components of the nail enamel allowing the components to flow onto the nail, and should be able to evaporate from the nail in a matter of minutes at room temperature and pressure Examples of preferred solvents include toluene, isopropanol, butyl acetate, ethyl acetate, glycol ethers, N-methyl pyrrolidone, alkyl lactates, and mixtures thereof. Effective amounts of the solvent component will generally lie in the range of about 40 wt. % to about 60 wt. % of the composition.

A suspending agent is an optional, but preferred, component of the nail enamel compositions of the present invention. The suspending agent should help suspend the pigments in the nail enamel, and helps adjust the viscosity to achieve desired flowability. Examples of preferred suspending agents include montmorillonite clays, and treated clays such as stearalkonium hectorite. The amount of the suspending agent can of course depend on the desired flow characteristics of the nail enamel, but amounts on the order of about 0.5 to about 2 wt. % are generally satisfactory.

The nail enamel compositions of the present invention can be clear, i.e. unpigmented, or they can include a pigment component. Suitable pigments include all inorganic and organic pigments which are usable in cosmetic formulations. Particular examples include carmine, bismuth oxychloride, zinc oxide, ferric oxide, ferrous oxide, kaolin, ultramarine violet, ultramarine blue, chromium oxide, chromium hydroxide, silica, and manganese violet. Other examples include lakes of organic colorants such as D&C Red No.. 7 Calcium Lake, FD&C Yellow No. 5 Aluminum and Zirconium Lakes, D&C Red No. 6 and No. 9 Barium Lakes, D&C Red #34 Calcium Lake, and D&C Red No. 30. Additional examples include talc, mica, titanium dioxide; any of the foregoing carried on the surface of talc, mica or titanium dioxide; and titanated mica.

The term "pigment" includes mixtures of two or more of the foregoing, and includes any of the foregoing the surfaces of which have been treated by the addition of silicone, lecithin, or other surface treatments.

The amounts of any particular ingredients comprising the pigment component will of course depend on the shade desired by the practitioner. In general, the pigment component comprises about 0.01 to about 10 wt. % of the composition.

Optionally, one may include another plasticizer, such as e.g. an alkyl, alkylaryl, or cycloalkyl phthalate, though this is not necessary.

Nail enamels in accordance with the present invention can be manufactured by thoroughly and intimately mixing together all the components indicated above, in the amounts described above. Examples of satisfactory equipment and how to use it are readily apparent to one of ordinary skill in this art.

The preferred mixing procedure, especially when the plasticizer is glyceryl tribenzoate, is first to mix the plasticizer into a solution or to mix it into a solution to which only the film-forming component has already been added, and thereafter to mix in the other ingredients of the nail enamel. This procedure is preferred also whenever the plasticizer is relatively difficult to solubilize.

Nail enamels having the foregoing composition exhibit highly desirable properties, including long wear, long retention of flexibility and adherence, resistance to chipping, and high gloss. In addition, the presence of halogen substituents such as —F or —Cl is associated with reduced flammability of the composition. It is a notable advantage of the present invention that nail enamels in accordance with the foregoing description exhibit these properties even without the presence of phthalate plasticizing compounds and even without aldehyde-based condensation polymeric resins such as toluenesulfonamide-formaldehyde resins. Such components may be present, though, within the present invention. Thus, when nail enamels in accordance with the present invention are manufactured without the addition of any phthalates or aldehyde resins, the nail enamels possess the additional significant advantages of freedom from fugitive trace amounts of those additives or of unreacted free aldehyde.

The alkenyl groups in the compounds of formulas (I)–(V) permit formulation of nail enamel compositions which are cured to a desired film on the nail by exposure to actinic radiation and in particular to ultraviolet radiation.

The present invention will be described further in the following examples, which are intended for purposes of illustration and not limitation.

Preferred formulation parameters are set forth in the following Table I:

TABLE I

| INGREDIENT | FORMULATION A | FORMULATION B |
| --- | --- | --- |
| Nitrocellulose | 15–20 wt. % | 15–20 wt. % |
| Diester or triester Formula (I)–(IV) | 20–25 wt. % | 10–25 wt. % |
| Stearalkonium hectorite | 1–1.5 wt. % | 1–1.5 wt. % |
| Pigments | 0.01–10 wt. % | 0.01–10 wt. % |
| Solvent Component | 55–60 wt. % | 40–60 wt. % |

The following are additional specific examples of nail enamel formulations within the scope of the present invention:

| INGREDIENT | AMOUNT (wt. %) |
| --- | --- |
| CLEAR TOPCOAT | |
| Nitrocellulose | 20.0 |
| Glyceryl triacetylricinoleate | 5.0 |
| Toluene | 60.0 |
| Butyl acetate | 10.0 |
| Ethyl acetate | 5.0 |
| RED NAIL ENAMEL | |
| Nitrocellulose (¼" RS) | 15.00 |
| Glyceryl tribenzoate | 25.00 |
| Stearalkonium hectorite | 1.00 |
| Toluene | 42.63 |
| Isopropanol | 0.50 |
| Butyl acetate | 10.00 |
| Ethyl acetate | 5.00 |
| FD&C Red #6 Ba lake | 0.22 |
| FD&C Red #7 Ca lake | 0.35 |
| D&C Yellow #5 Zr lake | 0.05 |
| Titanium dioxide | 0.18 |
| Red Iron Oxide | 0.02 |
| Guanine | 0.05 |
| BERRY NAIL ENAMEL | |
| Nitrocellulose (¼" RS) | 15.00 |
| Nitrocellulose (½" RS) | 5.00 |
| Dipropylene Glycol Di-P-Aminobenzoate | 10.00 |
| Neopentyl Glycol Dioctanoate | 5.00 |
| Toluene | 49.80 |
| Ethyl Acetate | 10.00 |
| N-Methyl-2-Pyrrolidone | 2.00 |
| Isopropanol | 0.50 |
| Stearalkonium Hectorite | 1.00 |
| Titanium Dioxide | 0.30 |
| Black Iron Oxide | 0.30 |
| D&C Red #7 Ca Lake | 0.30 |
| D&C Red #34 Ca Lake | 0.30 |
| D&C Yellow #5 Zr Lake | 0.50 |
| TAUPE NAIL ENAMEL | |
| Nitrocellulose (¼" RS) | 20.00 |
| Neopentyl Glycol Dibenzoate | 15.00 |
| Glyceryl Triacetate | 5.00 |
| Toluene | 42.54 |
| Butyl Acetate | 10.00 |
| Ethyl Acetate | 5.00 |
| Isopropanol | 0.50 |
| Stearalkonium Hectorite | 1.00 |
| Titanium Dioxide | 0.75 |
| Brown Iron Oxide | 0.10 |
| Black Iron Oxide | 0.05 |
| D&C Yellow #5 Zr Lake | 0.05 |
| D&C Red #6 Ba Lake | 0.01 |
| MAUVE NAIL ENAMEL | |
| Nitrocellulose (¼" RS) | 15.00 |
| Nitrocellulose (½" RS) | 5.00 |
| Triisostearyl Trimerate | 15.00 |
| Toluene | 47.67 |
| Butyl Acetate | 10.00 |
| Ethyl Acetate | 5.00 |
| Isopropanol | 0.50 |
| Stearalkonium Hectorite | 1.00 |
| Titanium Dioxide | 0.65 |
| D&C Red #6 Ba Lake | 0.10 |
| D&C Red #34 Ca Lake | 0.05 |

-continued

| INGREDIENT | AMOUNT (wt. %) |
| --- | --- |
| Black Iron Oxide | 0.02 |
| D&C Yellow #5 Zr Lake | 0.01 |

What is claimed is:

1. A formaldehyde free nail enamel comprising a film forming component, a solvent component, and a plasticizer component, where the plasticizer component comprises one or more compounds of the formula:

$$R_1-C(O)-OCH_2-C(CH_3)_2-CH_2O-C(O)R_2 \quad (III)$$

wherein $R_1$ and $R_2$ are the same or different and represent (i) linear or branched alkyl having 1 to 35 carbon atoms, cyclic alkyl having 3 to 8 carbon atoms, or linear or branched alkenyl having 2 to 35 carbon atoms, any of the foregoing being unsubstituted or substituted with one, two or three groups selected from the group consisting of —CN, —SCN, —OH, —SH, —NH$_2$, —CONH$_2$, and —NO$_2$;

(ii) —X—C(O)O—A or —X—O—C(O)—A in which X is a straight or branched alkyl or alkenyl bridge containing up to 8 carbon atoms or is a phenyl ring —C$_6$H$_4$—, and A is phenyl, straight or branched alkyl having 1 to 35 carbon atoms, or straight or branched alkylene having 2 to 35 carbon atoms, wherein when X or A is alkenyl or alkenyl it is optionally substituted with —CN, —SCN, —NO$_2$, —OH, —SH, —NH$_2$ or —CONH$_2$ and wherein when X or A is phenyl it is optionally substituted with one, two or three substituents selected from the group consisting of
—CN, —SCN, —Cl, —Br, —F, —OCH$_3$, —OC$_2$H$_5$, OC$_6$H$_5$, —CH=CH$_2$, C$_{1-6}$alkyl, —CH$_2$CH=CH$_2$, —NO$_2$, —NH$_2$, —OH, —SH, and —SO$_2$NH$_2$;
is a phenyl ring —CH$_6$H$_4$—, and A is phenyl straight or branched alkyl having 1 to 35 carbon atoms, or straight or branched alkylene having 2 to 35 carbon atoms, (iii) a dimer or trimer acyl group; or (iv) BZ;

wherein BZ is a phenyl ring which is unsubstituted; or substituted with one or two groups of the formula —C(O)OR$_5$ wherein R$_5$ is phenyl, straight or branched alkyl containing 1 to 35 carbon atoms, or straight or branched alkenyl containing 2 to 35 carbon atoms, the alkyl and alkenyl optionally substituted with —CN, —SCN, —NO$_2$, —OH, —SH, —NH$_2$ or —CONH$_2$; or substituted with one, two or three substituents selected from the group consisting of
—CN, —SCN, —Cl, —Br, —F, —OCH$_3$, —OC$_2$H$_5$, —OC$_6$H$_5$,
—CH=CH$_2$, C$_{1-6}$alkyl —CH$_2$CH=CH$_2$, —NO$_2$, NH$_2$, —OH, —SH, and —SO$_2$NH$_2$.

2. A nail enamel according to claim 1 wherein $R_1$, and $R_2$ are the same.

3. A nail enamel according to claim 1 wherein $R_1$ and $R_2$ are unsubstituted.

4. A nail enamel according to claim 1 wherein $R_1$ and $R_2$ represent linear or branched alkyl having 1 to 18 carbon atoms, or linear or branched alkenyl having 2 to 18 carbon atoms and are unsubstituted or substituted.

5. A nail enamel according to claim 1 wherein $R_1$ and $R_2$ are BZ.

6. A nail enamel according to claim 1 wherein the plasticizer component comprises about 0.5 wt. % to about 40 wt. % of the nail enamel.

7. A nail enamel according to claim 1 wherein the film-forming component comprises about 10 wt. % to about 40 wt. % of the nail enamel.

8. A nail enamel according to claim 1 wherein the plasticizer component is neopentyl benzoate.

* * * * *